United States Patent
Jang et al.

(10) Patent No.: US 9,916,974 B2
(45) Date of Patent: Mar. 13, 2018

(54) AMINO-SILYL AMINE COMPOUND AND THE MANUFACTURING METHOD OF DIELECTRIC FILM CONTAINING SI—N BOND BY USING ATOMIC LAYER DEPOSITION

(71) Applicant: DNF CO., LTD., Daejeon (KR)

(72) Inventors: Se Jin Jang, Daegu (KR); Sang-Do Lee, Daejeon (KR); Jong Hyun Kim, Daejeon (KR); Sung Gi Kim, Daejeon (KR); Sang Yong Jeon, Sejong (KR); Byeong-il Yang, Daejeon (KR); Jang Hyeon Seok, Daejeon (KR); Sang Ick Lee, Daejeon (KR); Myong Woon Kim, Daejeon (KR)

(73) Assignee: DNF CO., LTD., Daejeon (KR)

( * ) Notice: Subject to any disclaimer, the term of this patent is extended or adjusted under 35 U.S.C. 154(b) by 0 days.

(21) Appl. No.: 15/317,920

(22) PCT Filed: Jun. 4, 2015

(86) PCT No.: PCT/KR2015/005610
§ 371 (c)(1),
(2) Date: Dec. 9, 2016

(87) PCT Pub. No.: WO2015/190749
PCT Pub. Date: Dec. 17, 2015

(65) Prior Publication Data
US 2017/0125243 A1    May 4, 2017

(30) Foreign Application Priority Data

Jun. 11, 2014  (KR) .................. 10-2014-0070909
May 19, 2015  (KR) .................. 10-2015-0069444

(51) Int. Cl.
H01L 21/02       (2006.01)
C23C 16/455     (2006.01)
(Continued)

(52) U.S. Cl.
CPC ...... H01L 21/02219 (2013.01); C01B 21/068 (2013.01); C07F 7/10 (2013.01);
(Continued)

(58) Field of Classification Search
None
See application file for complete search history.

(56) References Cited

U.S. PATENT DOCUMENTS 5,413,813 A      5/1995   Cruse et al.
2005/0085054 A1  4/2005   Chakravarti et al.
(Continued)

FOREIGN PATENT DOCUMENTS

JP    2004281853 A    10/2004
KR   1020060103871 A  10/2006
(Continued)

OTHER PUBLICATIONS

Denis, J. et al., "First Evidence of Unhindered Silanimines Obtained by Flash Vacuum Thermolysis and Vacuum Gas-Solid Reaction," Chemische Berichte, vol. 125, No. 6, Jun. 1992, 4 pages.
(Continued)

*Primary Examiner* — Asok K Sarkar
(74) *Attorney, Agent, or Firm* — McCoy Russell LLP

(57) ABSTRACT

Provided are a novel amino-silyl amine compound and a manufacturing method of a dielectric film containing Si—N bond using the same. Since the amino-silyl amine compound according to the present invention, which is a thermally stable and highly volatile compound, may be treated at room temperature and used as a liquid state compound at room temperature and pressure, the present invention provides a (Continued)

manufacturing method of a high purity dielectric film containing a Si—N bond even at a low temperature and plasma condition by using atomic layer deposition (PEALD).

16 Claims, 4 Drawing Sheets

(51) Int. Cl.
    *C01B 21/068*     (2006.01)
    *C07F 7/10*     (2006.01)
    *C23C 16/34*     (2006.01)

(52) U.S. Cl.
    CPC ...... *C23C 16/345* (2013.01); *C23C 16/45536* (2013.01); *C23C 16/45553* (2013.01); *H01L 21/0217* (2013.01); *H01L 21/0228* (2013.01); *H01L 21/02274* (2013.01)

(56) References Cited

U.S. PATENT DOCUMENTS

2009/0087561 A1     4/2009   Chen et al.
2016/0237100 A1*   8/2016   Spence ............... C01B 21/0823

FOREIGN PATENT DOCUMENTS

| KR | 1020110132534 A | 12/2011 |
| KR | 1020120098448 A | 9/2012 |
| WO | 2013177326 A | 11/2013 |

OTHER PUBLICATIONS

Xiao, Y. et al., "Synthetic Approaches to Cyclodisilazanes and Branched Silazanes," Organometallics, vol. 23, No. 9, Sep. 13, 2004, Available Online Aug. 18, 2004, 7 pages.

ISA Korean Intellectual Property Office, International Search Report Issued in Application No. PCT/KR2015/005610, dated Sep. 10, 2015, WIPO, 2 pages.

* cited by examiner

AMINO-SILYL AMINE COMPOUND AND THE MANUFACTURING METHOD OF DIELECTRIC FILM CONTAINING SI—N BOND BY USING ATOMIC LAYER DEPOSITION

CROSS-REFERENCE TO RELATED APPLICATIONS

The present application is a U.S. National Phase of International Patent Application Serial No. PCT/KR2015/005610, entitled "NOVEL AMINO-SILYL AMINE COMPOUND AND THE MANUFACTURING METHOD OF DIELECTRIC FILM CONTAINING SI-N BOND BY USING ATOMIC LAYER DEPOSITION," filed on Jun. 4, 2015. International Patent Application Serial No. PCT/KR2015/005610 claims priority to Korean Patent Application No. 10-2014-0070909, filed on Jun. 11, 2014; and to Korean Patent Application No. 10-2015-0069444, filed on May 19, 2015. The entire contents of each of the above-cited applications are hereby incorporated by reference for all purposes.

TECHNICAL FIELD

The present invention relates to a novel amino-silyl amine compound and a manufacturing method of a dielectric film containing a Si—N bond by using atomic layer deposition, and more particularly, to a manufacturing method of a dielectric film containing a Si—N bond manufactured by adjusting ratios and amounts of an amino-silyl amine compound, a reaction gas containing a nitrogen source, and argon gas using atomic layer deposition.

BACKGROUND ART

A dielectric film containing a Si—N including a silicon nitride (SiN) film and a silicon carbonitride (SiCN) film has high resistance against hydrogen fluoride (HF). Therefore, in a manufacturing process of a semiconductor device such as a memory, a large scale integrated circuit (LSI), and the like, the dielectric film may be used as an etching stopper layer at the time of etching a silicon oxide ($SiO_2$) film, or the like, a film for preventing a deviation increase of resistance of a gate electrode or diffusion of a dopant, or the like. Particularly, there is a need to decrease a film formation temperature of a silicon nitride film after forming the gate electrode. For example, at the time of forming the silicon nitride film after forming the gate electrode, the film formation temperature should be lower than 760° C., which is a film formation temperature in the case of using low pressure-chemical vapor deposition (LP-CVD) according to the related art, or 550° C., which is a film formation temperature in the case of using atomic layer deposition (ALD).

The ALD is a method of alternately supplying one of two kinds (or more) of source gas used for film formation onto a substrate under arbitrary film formation conditions (temperature, time, and the like) to adsorb the gas in a unit of one atomic layer, and performing film formation using a surface reaction. For example, a film having a thickness corresponding to one molecular layer is formed by alternately flowing first source gas and second source gas along a surface of an object to be treated to adsorb source gas molecules of the first source gas in the surface of the object to be treated and reacting source gas molecules of the second source gas with the adsorbed source gas molecules of the first source gas. In addition, a film having high quality is formed on the surface of the object to be treated by repeating this step.

A silicon nitride film capable of being formed at a low temperature of 300° C. to 600° C. by supplying an ammonia radical ($NH_3$*) obtained by activating ammonia with plasma in the case of alternatively supplying dichlorosilane (DCS: $SiH_2Cl_2$) and ammonia ($NH_3$) using ALD has been disclosed in Japanese Patent Laid-Open Publication No. 2004-281853. However, in the silicon nitride film formed at a low temperature using ALD, a concentration of chlorine (Cl) that is a factor affecting natural oxidation of the silicon nitride film or deteriorating resistance of the silicon nitride film against hydrogen fluoride is increased, such that a wet etch rate is large, and thus, etching selectivity (selection rate) to an oxide film is small. Further, the silicon nitride film formed at a low temperature has low film stress, such that it is impossible to implement desired stress intensity. A method of introducing carbon (C) in the silicon nitride film to improve resistance against hydrogen fluoride may be suggested, but in a low temperature region of 400° C. or less, introduction of carbon in the silicon nitride film may cause a structural defect, such that a dielectric property may be deteriorated.

Therefore, the present inventors tried to provide a manufacturing method of a dielectric film containing a Si—N bond having excellent cohesive force, a high deposition rate, and excellent physical and electrical properties even at a low temperature by using atomic layer deposition, thereby completing the present invention.

RELATED ART DOCUMENT

Patent Document

Korean Patent Laid-Open Publication No. 10-2006-0103871
Korean Patent Laid-Open Publication No. 10-2012-0098448
Japanese Patent Laid-Open Publication No. 2004-281853

DISCLOSURE

Technical Problem

An object of the present invention is to provide an amino-silyl amine compound having excellent thermal stability and high reactivity, and a manufacturing method of a dielectric film containing a Si—N bond manufactured by adjusting a ratio of the amino-silyl amine compound and a reaction gas containing a nitrogen source using atomic layer deposition.

Technical Solution

In one general aspect, there is provided an amino-silyl amine compound represented by the following Chemical Formula 1.

[Chemical Formula 1]

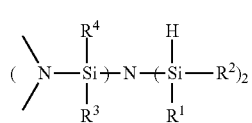

[In Chemical Formula 1,
$R^1$ to $R^4$ are each independently hydrogen, (C1-C3)alkyl, (C2-C3)alkenyl, (C2-C3)alkynyl, (C3-C7)cycloalkyl, or (C6-C12) aryl.]

$R^1$ to $R^4$ may each independently hydrogen, methyl, or vinyl.

The amino-silyl amine compound represented by Chemical Formula 1 may be selected from the following compounds.

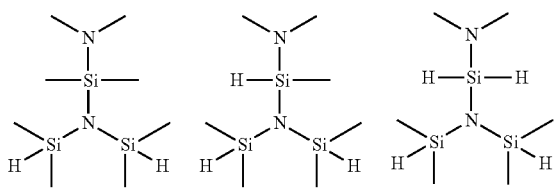

In another general aspect, there is provided a composition for silicon-containing dielectric film deposition, containing an amino-silyl amine compound represented by the following Chemical Formula 2.

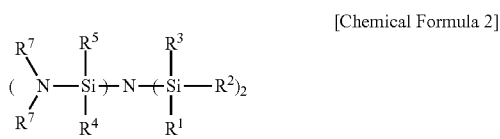

[Chemical Formula 2]

[In Chemical Formula 2,
$R^1$ to $R^7$ are each independently hydrogen, (C1-C4)alkyl, (C2-C4)alkenyl, (C2-C4)alkynyl, (C3-C10)cycloalkyl, or (C6-C12) aryl.]

The amino-silyl amine compound represented by Chemical Formula 2 may be selected from the following compounds.

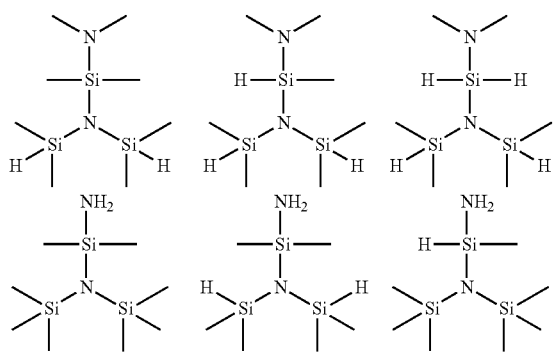

In another general aspect, there is provided a manufacturing method of a dielectric film containing a Si—N bond using the composition for silicon-containing dielectric film deposition.

The manufacturing method of a dielectric film may include: a) contacting the composition for silicon-containing dielectric film deposition with a substrate to adsorb the composition for silicon-containing dielectric film deposition in the substrate; b) purging the remaining composition for silicon-containing dielectric film deposition and by-products; c) forming an atomic layer having a Si—N bond by injecting reaction gas into the substrate containing the adsorbed composition for silicon-containing dielectric film deposition to remove a ligand of the composition for silicon-containing dielectric film deposition; and d) purging the remaining reaction gas and reaction by-products.

The manufacturing method of a dielectric film may include: a) contacting the composition for silicon-containing dielectric film deposition with a substrate to adsorb the composition for silicon-containing dielectric film deposition in the substrate; b) purging the remaining composition for silicon-containing dielectric film deposition and by-products; c') forming an atomic layer having a Si—N bond by generating plasma while injecting reaction gas into the substrate containing the adsorbed composition for silicon-containing dielectric film deposition to remove a ligand of the adsorbed composition for silicon-containing dielectric film deposition; and d) purging the remaining reaction gas and reaction by-products.

The reaction gas may be supplied after being activated by generating plasma of 50 to 1000 W.

The reaction gas may be supplied after being activated by generating plasma of 100 to 500 W.

A substrate temperature may be 100 to 600° C.

The reaction gas may be supplied at a flow rate of 100 to 10000 sccm.

Step a) may be performed at a pressure of 0.05 to 10 torr, and step c) and step c') may be performed at a pressure of 0.05 to 30 torr.

Advantageous Effects

A novel amino-silyl amine compound according to the present invention has excellent thermal stability and high reactivity, and a silicon-containing film manufactured using this amino-silyl amine compound as a precursor has high purity and excellent physical and electrical properties, such that the amino-silyl amine compound may be used as a composition for silicon-containing dielectric film deposition capable of forming a silicon-containing dielectric film in a low temperature region.

In addition, a dielectric film manufactured using the composition for silicon-containing dielectric film deposition containing the amino-silyl amine compound has high purity and excellent physical and electrical properties, and a dielectric film containing Si—N bond, having high stress at a low temperature may be manufactured by using atomic layer deposition.

DESCRIPTION OF DRAWINGS

The above and other objects, features and advantages of the present invention will become apparent from the following description of preferred embodiments given in conjunction with the accompanying drawings, in which.

BEST MODE

Figure 1:
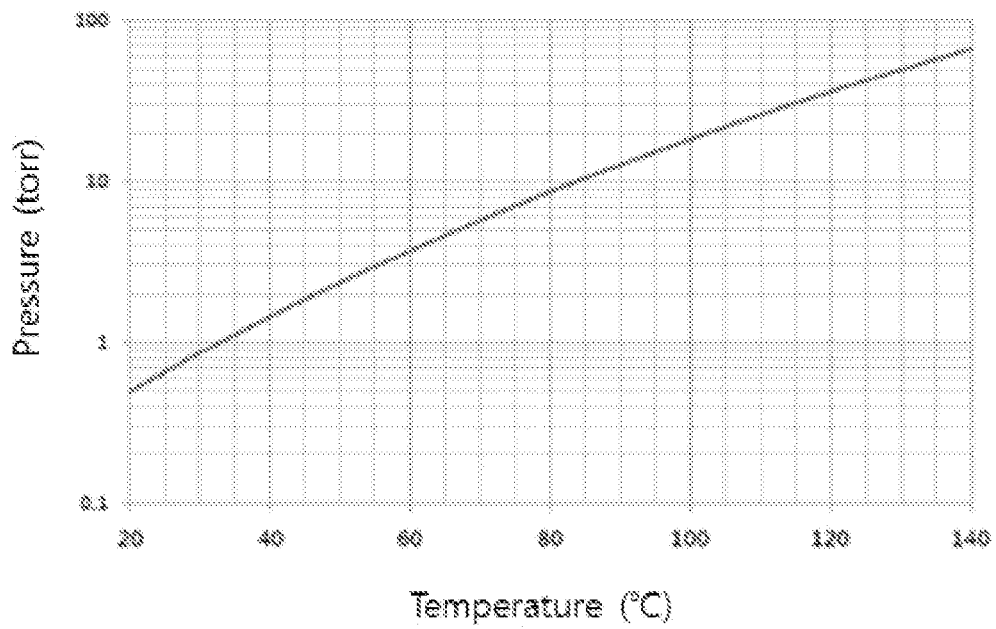
FIG. 1 illustrates a result obtained by measuring a vapor pressure of a novel amino-silyl amine compound prepared in Example 1.

The present invention provides a novel amino-silyl amine compound capable of forming a dielectric film containing a Si—N bond having excellent cohesive force, a high deposition rate, and excellent physical and electrical properties even at a low temperature, and a manufacturing method of a dielectric film containing Si—N bond by using atomic layer deposition.

The amino-silyl amine compound according to the present invention may be represented by the following Chemical Formula 1.

[Chemical Formula 1]

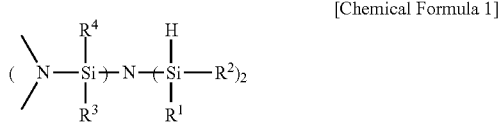

[In Chemical Formula 1,
$R^1$ to $R^4$ are each independently hydrogen, (C1-C3)alkyl, (C2-C3)alkenyl, (C2-C3)alkynyl, (C3-C7)cycloalkyl, or (C6-C12) aryl.]

As disclosed herein, the terms ⌈alkyl⌋ and other substituents including an ⌈alkyl⌋ part include both of the straight chain type and the branched chain type. In addition, as disclosed herein, the term ⌈aryl⌋, which is an organic radical derived from an aromatic hydrocarbon by removing one hydrogen, includes a single or fused ring system containing, properly 4 to 7 ring atoms, and preferably 5 or 6 ring atoms in each ring, and include a plurality of aryl groups linked with a single bond(s). A specific example of aryl includes phenyl, naphthyl, biphenyl, anthryl, indenyl, fluorenyl, or the like, but is not limited thereto. Further, ⌈alkenyl⌋ of the present invention is linear or branched hydrocarbon including at least one double bond, and a specific example thereof may include vinyl, prop-1-en, or buta-1,3-diene, but the present invention is not limited thereto. In addition, ⌈alkynyl⌋ of the present invention includes linear or branched hydrocarbon including at least one triple bond.

The novel amino-silyl amine compound according to the present invention, which is a compound in a liquid state at room temperature and pressure, has excellent volatility, at the time of manufacturing a dielectric film, the amino-silyl amine compound may be rapidly and easily deposited and have excellent cohesive force and step coverage.

In addition, due to a trigonal planar molecular structure of $Si_3N$ in which three silicon atoms are bonded to a central nitrogen atom, the amino-silyl amine compound according to the present invention has high thermal stability, low activation energy, excellent reactivity, and does not produce by-products, which are non-volatile, such that a high purity silicon-containing dielectric film may be easily formed.

In the amino-silyl amine compound represented by Chemical Formula 1 according to an exemplary embodiment of the present invention, preferably, $R^1$ to $R^4$ in Chemical Formula 1 may be each independently hydrogen, methyl, or vinyl, in view of forming a dielectric film having high thermal stability, reactivity and a high purity.

Further, in view of forming a dielectric film having excellent cohesive force and step coverage, it is more preferable that the amino-silyl amine compound represented by Chemical Formula 1 is selected from the following compounds, but the present invention is not limited thereto.

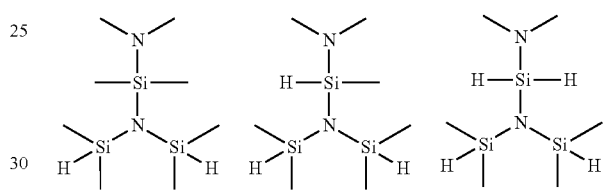

In addition, the present invention provides a composition for silicon-containing dielectric film deposition containing an amino-silyl amine compound represented by the following Chemical Formula 2, capable of forming a silicon film having excellent cohesive force, a high deposition rate, and excellent physical and electrical properties even at a low temperature.

[Chemical Formula 2]

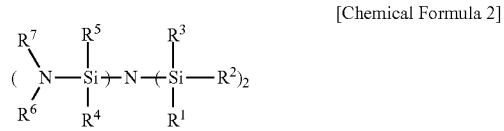

[In Chemical Formula 2,
$R^1$ to $R^7$ are each independently hydrogen, (C1-C4)alkyl, (C2-C4)alkenyl, (C2-C4)alkynyl, (C3-C10)cycloalkyl, or (C6-C12) aryl.]

The composition for silicon-containing dielectric film deposition according to the present invention may contain the amino-silyl amine compound represented by Chemical Formula 2 as a precursor for dielectric film deposition, and a content of the amino-silyl amine compound in the composition may be in a range recognized by a person skilled in the art in consideration of film formation conditions, a thickness, properties, and the like, of the dielectric film.

In view of decreasing a wet etch rate, the amino-silyl amine compound contained in the composition for silicon-containing dielectric film deposition as the precursor for dielectric film deposition may be preferably selected from the following compounds, but is not limited thereto.

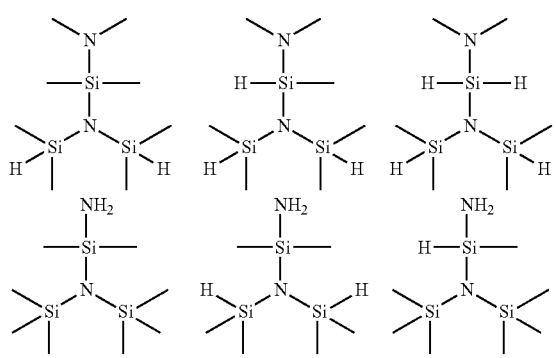

The present invention provides a manufacturing method of a dielectric film containing a Si—N bond using the composition for silicon-containing dielectric film deposition.

The manufacturing method of a dielectric film may include: a) contacting the composition for silicon-containing dielectric film deposition with a substrate to adsorb the composition for silicon-containing dielectric film deposition in the substrate; b) purging the remaining composition for silicon-containing dielectric film deposition and by-products; c) forming an atomic layer having a Si—N bond by injecting reaction gas into the substrate containing the adsorbed composition for silicon-containing dielectric film deposition to remove a ligand of the composition for silicon-containing dielectric film deposition; and d) purging the remaining reaction gas and reaction by-products.

In addition, the manufacturing method of a dielectric film may include: a) contacting the composition for silicon-containing dielectric film deposition with a substrate to adsorb the composition for silicon-containing dielectric film deposition in the substrate; b) purging the remaining composition for silicon-containing dielectric film deposition and by-products; c') forming an atomic layer having a Si—N bond by generating plasma while injecting reaction gas to remove a ligand of the adsorbed composition for silicon-containing dielectric film deposition; and d) purging the remaining reaction gas and reaction by-products.

It is preferable that the manufacturing method of a dielectric film is performed under an inert atmosphere. Further, in order to manufacture a dielectric film having high purity, the manufacturing method may further include, after performing step a), removing an extra amino-silyl amine compound that is not adsorbed in the substrate and by-products generated during an adsorption process.

The forming of the atomic layer having a Si—N bond by generating plasma while injecting the reaction gas to remove the ligand of the adsorbed composition for silicon-containing dielectric film deposition (step c') may include a process of injecting reaction gases in a chamber, generating at least one reaction gas radical of the reaction gases activated using plasma, converting the amino-silyl amine compound adsorbed by the activated reaction gas radical into silicon nitride (SiN), silicon carbonitride (SiCN), or silicon oxynitride (SiON), and then depositing a dielectric film including a Si—N bond on the substrate and a process of removing the ligand of the composition for silicon-containing dielectric film deposition generated during the process of converting the amino-silyl amine compound into silicon nitride (SiN), silicon carbonitride (SiCN), or silicon oxynitride (SiON).

In addition, a cycle may be repeatedly performed until the desired thickness of the atomic layer having the Si—N bond is obtained.

A substrate temperature may be 100 to 600° C., preferably 100 to 550° C. This means that the atomic layer may be formed even by a low temperature process by using the amino-silyl amine compound having excellent volatility.

A pressure at the time of forming the atomic layer may be 0.05 to 30 torr. Preferably, in step a), the pressure may be 0.05 to 10 torr, and in step c) and step c'), the pressure may be 0.05 to 30 torr.

The substrate temperature may be 100° C. to 600° C., and the reaction gas may be at least one nitrogen source reaction gas selected from nitrogen ($N_2$), ammonia ($NH_3$), $N_2O$, NO, and $NO_2$, but is not limited thereto. In this case, it is preferable that the reaction gas is supplied at a flow rate of 100 to 10000 standard cubic centimeter per minute (sccm), and it is preferable that the reaction gas in step c') is supplied after being activated by generating plasma in a range of 50 to 1000 W.

In the case of the dielectric film manufactured by the manufacturing method according to the present invention, the dielectric film may have an excellent deposition rate and high stress only by supplying lower-temperature and low-power plasma, and a content of carbon may be minimized, such that a high quality dielectric film having a Si—N bond may be formed. Preferably, the dielectric film may be manufactured by generating plasma of 50 to 800 W. More preferably, the dielectric film may be manufactured by generating low-power power plasma of 100 to 500 W.

In addition, the present invention provides a dielectric film containing a Si—N bond manufactured by using the amino-silyl amine compound as a precursor. The dielectric film uses the amino-silyl amine compound according to the present invention, such that the dielectric film may have high stress at a low temperature and a rapid deposition rate due to low activation energy of the amino-silyl amine compound, and non-volatile by-products are hardly generated, and thus, the dielectric film may have a high purity.

Hereinafter, the present invention will be described in more detail based on the following Examples. However, the following Examples are to illustrate the present invention, but the present invention is not limited thereto.

The following Examples of all compounds were practiced under anhydrous and inert atmosphere using a glove box or a Schlenk pipe, products were analyzed by $^1H$ nuclear magnetic resonance (NMR), thermogravimetric analysis (TGA), and gas chromatography (GC), deposition was performed using a commercialized showerhead type single wafer type atomic layer deposition (ALD) apparatus (200 mm) and plasma enhanced atomic layer deposition (PEALD) known in the art, each thickness of deposited dielectric films was measured by Ellipsometer, and deposited films and compositions thereof were analyzed by infrared spectroscopy and Auger electron spectroscopy (AES).

[Example 1] Synthesis of dimethylaminodimethylsilyl bisdimethylsilyl amine 400 g (4.23 mol) of chlorodimethylsilane(($CH_3)_2HSiCl$) and 1500 ml of n-pentane (organic solvent) were put into in a 3000 mL flame-dried Schlenk flask under anhydrous and inert atmosphere while stirring, and 216 g (12.68 mol) of ammonia ($NH_3$) was slowly added thereto while maintaining a temperature at −25° C. After the addition was completed, the reaction solution was slowly heated to room temperature and stirred for 6 hours. The produced white solid was removed by filtering the reaction mixture after reaction was terminated, thereby obtaining a filtrate. Then, a solvent was removed from this filtrate under reduced pressure, thereby recovering 197 g (1.48 mol) of tetramethyldisilazane ((($CH_3$)$_2$HSi)$_2$NH). 197 g (1.48 mol) of the recovered tetramethyldisilazane ((($CH_3$)$_2$HSi)$_2$NH) and 300 ml of n-hexane (organic solvent) were put into a 2000 mL flame-dried Schlenk flask while stirring, and 456 g (1.48 mol) of 2.29M normal butyl lithium (n-$C_4H_9$Li) hexane ($C_6H_{14}$) solution was slowly added thereto while maintaining a temperature at −15° C. After the addition was completed, the reaction solution was slowly heated to room temperature and stirred for 12 hours. Then, 500 ml of tetrahydrofuran (O($C_2H_2$)$_2$) was added thereto. 203 g (1.48 mol) of chlorodi ethyl dimethylaminosilane (ClSi($CH_3$)$_2$(N($CH_3$)$_2$)) synthesized by reacting dichloro dimethylsilane ($Cl_2$Si($CH_3$)$_2$) with 2 equivalents of dimethylamine in a quantitative scheme was slowly added to the reaction solution while maintaining a temperature at −20° C. After the addition, the reaction solution was slowly heated, and stirred for 12 hours while maintaining the temperature at 65° C. The produced white solid was removed by filtering the reaction mixture after the reaction was terminated, thereby obtaining a filtrate. A solvent was removed from this filtrate under reduced pressure, and 208 g (0.89 mol) of dimethylaminodimethylsilyl bisdimethylsilyl amine ((($CH_3$)$_2$SiH)$_2$N(Si($CH_3$)$_2$(N($CH_3$)$_2$)) was obtained with a yield of 60% through distillation under reduced pressure.

Figure 2:
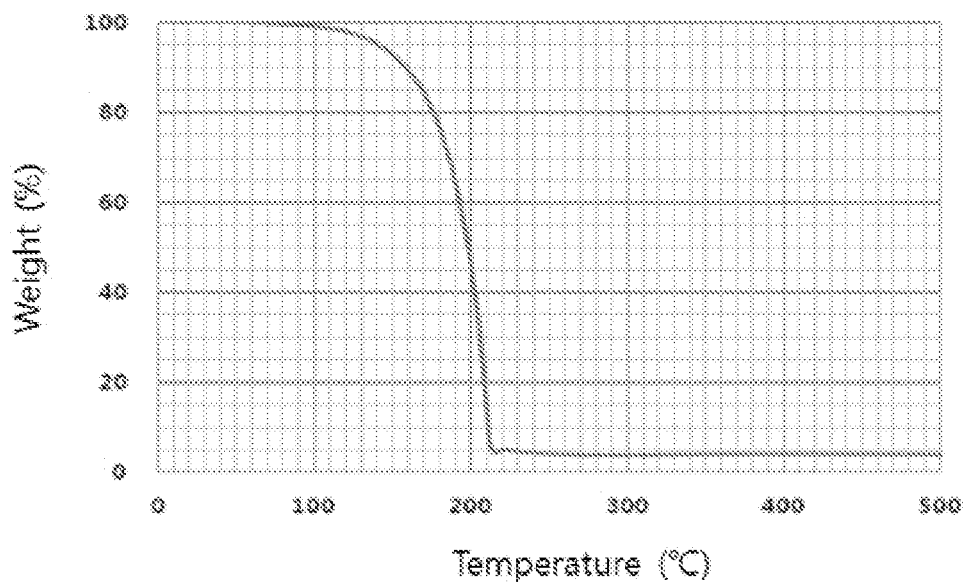
FIG. 2 illustrates a result obtained by performing thermogravimetric analysis on the novel amino-silyl amine compound prepared in Example 1.

A vapor pressure of dimethylaminodimethylsilyl bisdimethylsilyl amine ((($CH_3$)$_2$SiH)$_2$N(Si($CH_3$)$_2$(N($CH_3$)$_2$)) was measured and thermogravimetric analysis thereof was performed, and the results were illustrated in FIGS. 1 and 2.

$^1$H-NMR (in$C_6D_6$) δ 0.20 (s, 6H, NSi($CH_3$)$_2$N($CH_3$)$_2$), 0.23 (d, 12H, NSiH($CH_3$)$_2$), 2.46 (s, 6H, Si(N($CH_3$)$_2$), 4.68 (m, 2H, NSiH($CH_3$)$_2$);

Boiling point: 197° C.;

GC analysis result >99%.

[Example 2] Manufacturing of Dielectric Film Containing Si—N Bond by Using Plasma Enhanced Atomic Layer Deposition (PEALD)

Figure 3:
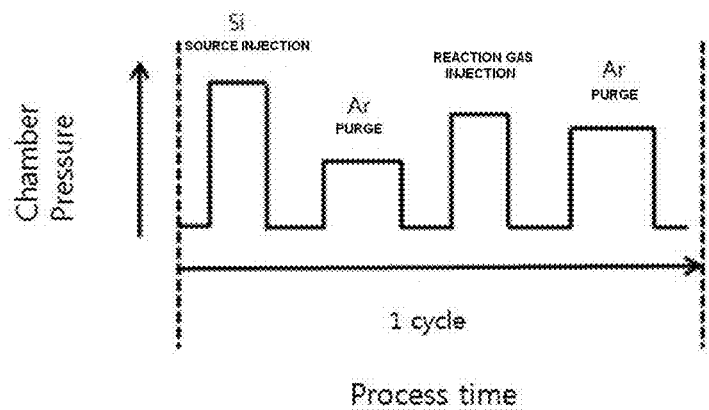
FIG. 3 is a view illustrating a deposition method of a dielectric film containing a Si—N bond performed in Example 2.
Figure 4:
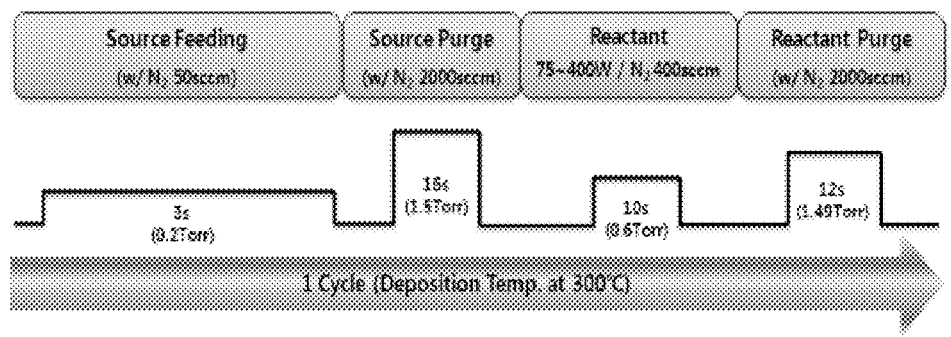
FIG. 4 is a view illustrating a deposition method of a dielectric film containing a Si—N bond performed in Examples 3 to 5.

A dielectric film containing a Si—N bond was formed at a silicon substrate temperature of 300° C. and plasma of 400 W using a composition for silicon-containing dielectric film deposition containing the compound of Example 1 in a general plasma enhanced atomic layer deposition (PEALD) apparatus using plasma enhanced atomic layer deposition (PEALD). A mixture in which nitrogen ($N_2$) and ammonia ($NH_3$) were mixed at a ratio of 200:30 was used as the reaction gas, and argon, which is inert gas, was used as purge gas. Hereinafter, a specific deposition method of a dielectric film containing a Si—N bond was illustrated in FIGS. 3 and 4 and Table 1.

A thickness of the dielectric film containing a Si—N bond deposited by the method of Example 2 was measured by ellipsometer and transmission electron microscope (TEM), and components of the dielectric film (silicon nitride film) were analyzed using infrared spectroscopy (IR), Auger electron spectroscopy (AES), and secondary ion mass spectrometer (SIMS). The results were illustrated in Table 2.

Figure 5:
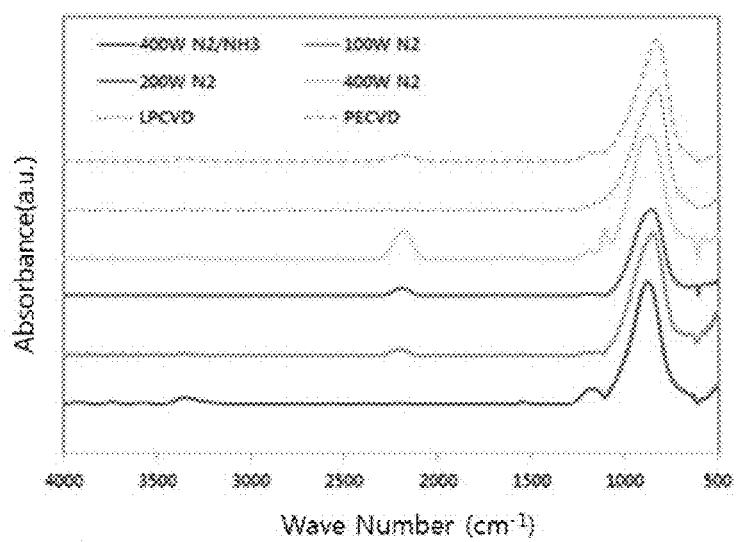
FIG. 5 illustrates a result obtained by analyzing the dielectric film containing a Si—N bond deposited in Example 2 using infrared spectroscopy.
Figure 6:
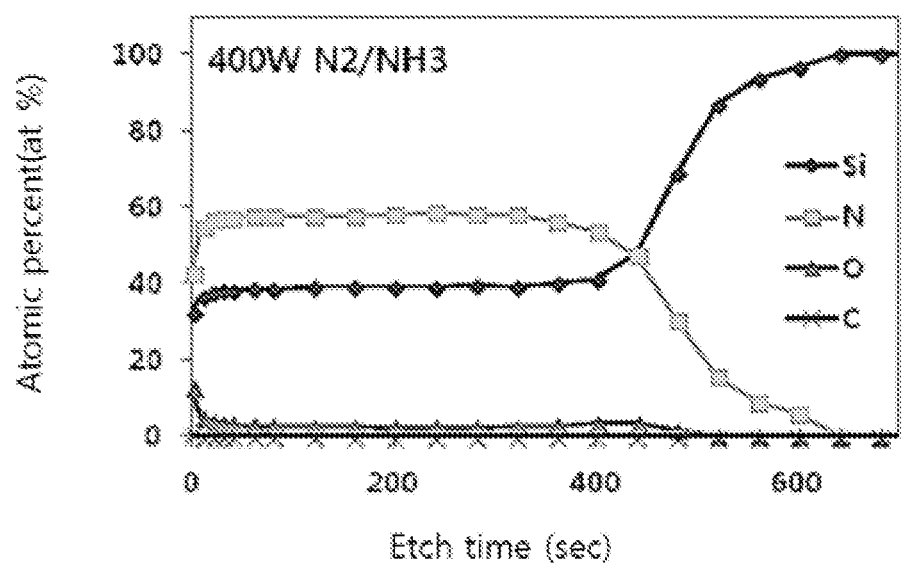
FIG. 6 illustrates a result obtained by analyzing a composition of the dielectric film containing a Si—N bond deposited in Example 2 using Auger electron spectroscopy.

FIGS. 5 and 6 illustrate results obtained by analyzing the dielectric film containing a Si—N bond deposited by the method of Example 2 and compositions thereof using infrared spectroscopy and Auger electron spectroscopy, respectively. Molecular vibration of Si—N was observed in a range of 850 to 868 $cm^{-1}$ in infrared spectra, and as a result of Auger electron spectroscopy, it was confirmed that a ratio of Si and N was in a range of 0.68 to 0.84. In addition, it may be appreciated that a high quality dielectric film containing a Si—N bond in which a content of carbon was less than 1% was formed.

[Example 3] Manufacturing of Dielectric Film Containing Si—N Bond by Using Plasma Enhanced Atomic Layer Deposition (PEALD)

A dielectric film containing a Si—N bond was formed at a silicon substrate temperature of 300° C. and plasma of 100 W using a composition for silicon-containing dielectric film deposition containing the compound of Example 1 in a general plasma enhanced atomic layer deposition (PEALD) apparatus using plasma enhanced atomic layer deposition (PEALD). Nitrogen ($N_2$) was used as reaction gas, and argon, which is inert gas, was used as purge gas. Hereinafter, a specific deposition method of a dielectric film containing a Si—N bond was illustrated in FIG. 4 and Table 1.

Figure 7:
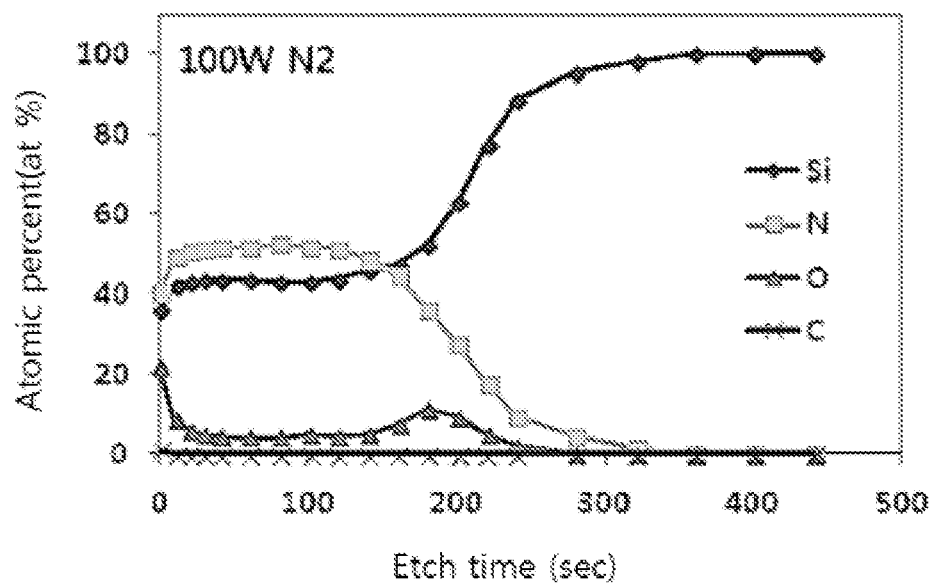
FIG. 7 illustrates a result obtained by analyzing a composition of the dielectric film containing a Si—N bond deposited in Example 3 using Auger electron spectroscopy.

Components of the dielectric film containing a Si—N bond deposited by the method of Example 3 were analyzed by the same method as in Example 2, and the results were illustrated in the following Table 2 (see FIG. 7).

[Example 4] Manufacturing of Dielectric Film Containing Si—N Bond by Using Plasma Enhanced Atomic Layer Deposition (PEALD)

A dielectric film containing a Si—N bond was formed at a silicon substrate temperature of 300° C. and plasma of 200 W using a composition for silicon-containing dielectric film deposition containing the compound of Example 1 in a general plasma enhanced atomic layer deposition (PEALD) apparatus using plasma enhanced atomic layer deposition (PEALD). Nitrogen ($N_2$) was used as reaction gas, and argon, which is inert gas, was used as purge gas. Hereinafter, a specific deposition method of a dielectric film containing a Si—N bond was illustrated in FIG. 4 and Table 1.

Figure 8:
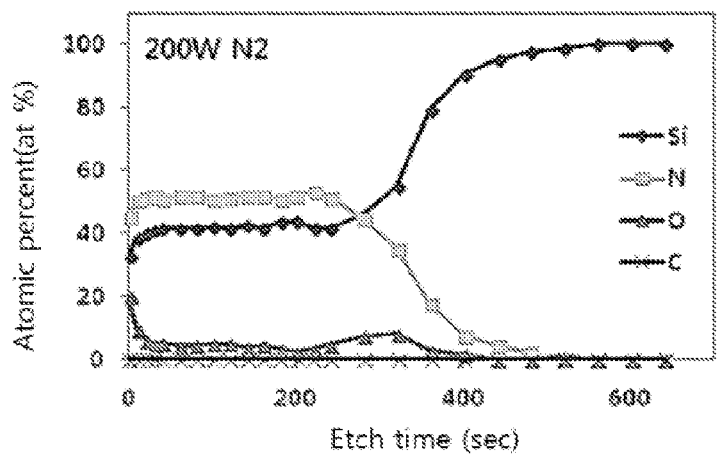
FIG. 8 illustrates a result obtained by analyzing a composition of the dielectric film containing a Si—N bond deposited in Example 4 using Auger electron spectroscopy.

Components of the dielectric film containing a Si—N bond deposited by the method of Example 4 were analyzed by the same method as in Example 2, and the results were illustrated in the following Table 2 (see FIG. 8).

[Example 5] Manufacturing of Dielectric Film Containing Si—N Bond by Using Plasma Enhanced Atomic Layer Deposition (PEALD)

A dielectric film containing a Si—N bond was formed at a silicon substrate temperature of 300° C. and plasma of 400 W using a composition for silicon-containing dielectric film deposition containing the compound of Example 1 in a general plasma enhanced atomic layer deposition (PEALD) apparatus using plasma enhanced atomic layer deposition (PEALD). Nitrogen ($N_2$) was used as reaction gas, and argon, which is inert gas, was used as purge gas. Hereinafter, a specific deposition method of a dielectric film containing a Si—N bond was illustrated in FIG. 4 and Table 1.

Figure 9:
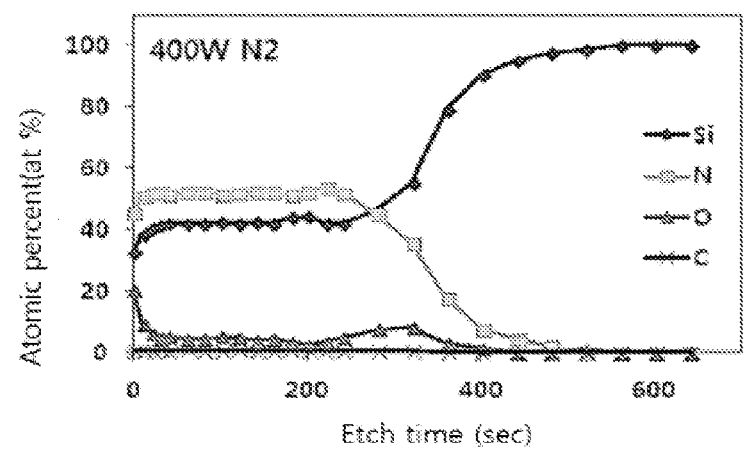
FIG. 9 illustrates a result obtained by analyzing a composition of the dielectric film containing a Si—N bond deposited in Example 5 using Auger electron spectroscopy.

Components of the dielectric film containing a Si—N bond deposited by the method of Example 5 were analyzed by the same method as in Example 2, and the results were illustrated in the following Table 2 (see FIG. 9).

Comparative Example 1

A dielectric film was manufactured using low pressure chemical vapor deposition (LPCVD) under conditions at which a substrate temperature was 700° C., a dichlorosilane (DCS) flow rate was 40 sccm, and an ammonia ($NH_3$) flow rate was 240 sccm. Hereinafter, a specific deposition method of a dielectric film was illustrated in Table 1, and components of the dielectric film were analyzed by the same method as in Example 2. The results were illustrated in the following Table 2.

Comparative Example 2

A dielectric film was manufactured using plasma enhanced chemical vapor deposition (PECVD) under conditions at which a substrate temperature was 400, plasma power was 500 W, and a ratio of silane (SiH$_4$) and ammonia (NH$_3$) was 1:8. Hereinafter, a specific deposition method of a dielectric film was illustrated in Table 1, and components of the dielectric film were analyzed by the same method as in Example 2. The results were illustrated in the following Table 2.

TABLE 1

|  |  | Example 2 | Example 3 | Example 4 | Example 5 |
|---|---|---|---|---|---|
| Precursor Heating Temperature (° C.) |  | 40 | 40 | 40 | 40 |
| Substrate Temperature (° C.) |  | 300 | 300 | 300 | 300 |
| Precursor Injection time (Second) |  | 6 | 3 | 3 | 3 |
| Purge | Flow Rate (sccm) | 1150 | 2000 | 2000 | 2000 |
|  | Time (second) | 20 | 16 | 16 | 16 |
| Reaction Gas and Plasma | Plasma Power (W) | 400 | 100 | 200 | 400 |
|  | N$_2$ Flow Rate (sccm) | 200 | 400 | 400 | 400 |
|  | NH$_3$ Flow Rate (sccm) | 30 | 0 | 0 | 0 |
|  | Time (second) | 10 | 10 | 10 | 10 |
| Purge | Flow Rate (sccm) | 1100 | 2000 | 2000 | 2000 |
|  | Time (second) | 15 | 12 | 12 | 12 |
| The Number of Deposition Cycle | Cycle | 600 | 500 | 500 | 500 |

|  |  | Deposition Conditions | | |
|---|---|---|---|---|
|  | Deposition Method | Substrate Temperature (° C.) | Plasma (W) | Reaction Gas |
| Comparative Example 1 | LPCVD | 770 | — | NH$_3$ |
| Comparative Example 2 | PECVD | 400 | 500 | NH$_3$ |

As a result, a deposition rate of the dielectric film containing a Si—N bond according to the present invention was in a range of 0.21 to 0.48 Å/cycle.

Figure 10:
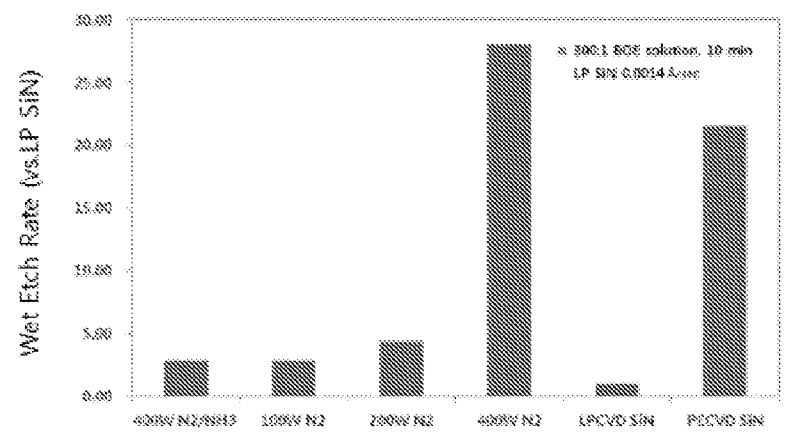
FIG. 10 illustrates a result obtained by analyzing resistance of the dielectric films containing a Si—N bond manufactured in Examples 2 to 5 and Comparative Examples 1 and 2 against hydrogen fluoride (300:1 BOE solution).

In addition, as illustrated in FIG. 10, resistance of the dielectric films containing a Si—N bond manufactured in Examples 2 to 5 against hydrogen fluoride (300:1 BOE solution) was compared with that of the dielectric film of Comparative Example 1 formed at a high temperature using the LPCVD method against hydrogen fluoride (300:1 BOE solution), and as a result, it may be confirmed that the resistance of the dielectric films in Examples 2 to 5 was 2.89 to 28.06 times higher than that in Comparative Example 1, such that resistance against hydrogen fluoride was excellent.

That is, in the case of using the composition for silicon-containing dielectric film deposition containing an amino-silyl amine compound through a plasma enhanced atomic layer deposition process, it was confirmed that the composition has a high utilization value in forming a high purity dielectric film containing Si—N bond capable of being deposited at a low temperature and low-power plasma, and may be usefully used across the whole application fields of the silicon-containing dielectric film.

The invention claimed is:

1. An amino-silyl amine compound represented by the following Chemical Formula 1:

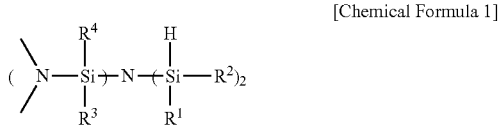

[Chemical Formula 1]

[In Chemical Formula 1,

R$^1$ to R$^4$ are each independently hydrogen, or (C1-C3)alkyl.]

2. The amino-silyl amine compound of claim 1, wherein R$^1$ to R$^4$ are each independently hydrogen, or methyl.

3. The amino-silyl amine compound of claim 1, wherein the amino-silyl amine compound represented by Chemical Formula 1 is selected from the following compounds

TABLE 2

|  | Deposition Rate (Å/cycle) | ✕Wet Etch Rate vs. LPCVD Si—N (0.014 Å/sec) | IR | | Film composition | | | H Content (%) |
|---|---|---|---|---|---|---|---|---|
|  |  |  | Si—N (cm−1) | Si—N/Si—H Ratio | Si/N Ratio | Oxygen atomic % | Carbon atomic % |  |
| Example 2 | 0.48 | 6.17 | 868 | 194.43 | 0.68 | 2.50 | 0.00 | 8.85 |
| Example 3 | 0.21 | 2.89 | 850 | 81.73 | 0.84 | 4.90 | 0.00 | 9.12 |
| Example 4 | 0.23 | 4.34 | 850 | 45.77 | 0.82 | 4.41 | 0.00 | 11.41 |
| Example 5 | 0.32 | 28.06 | 858 | 9.81 | 0.82 | 4.45 | 0.79 | 13.70 |
| Comparative Example 1 | — | 1.00 | 833 | — | 0.76 | 1.06 | 0.00 | 3.90 |
| Comparative Example 2 | — | 21.52 | 833 | 98.25 | 0.84 | 0.57 | 0.00 | 18.9 |

✕Wet etch rate: Value compared with a resistance result (0.014 Å/sec) of the dielectric film of Comparative Example 1 formed at a high temperature using the LPCVD against hydrogen fluoride (300:1 BOE solution).

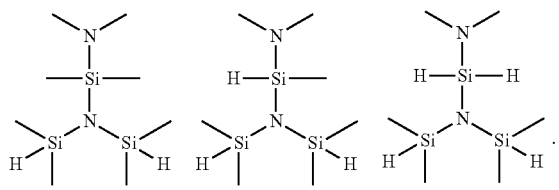

4. A composition for silicon-containing dielectric film deposition comprising an amino-silyl amine compound represented by the following Chemical Formula 2:

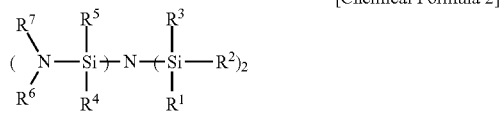

[Chemical Formula 2]

[In Chemical Formula 2, $R^1$ to $R^7$ are each independently hydrogen, or (C1-C4)alkyl.

5. The composition for silicon-containing dielectric film deposition of claim 4, wherein the amino-silyl amine compound represented by Chemical Formula 2 is selected from the following compounds

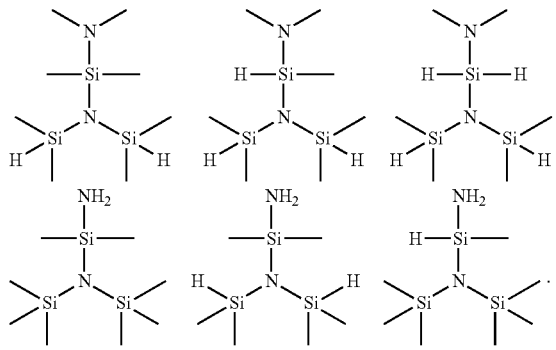

6. A manufacturing method of a dielectric film containing a Si—N bond, the manufacturing method using the composition for silicon-containing dielectric film deposition of claim 4 as a precursor.

7. The manufacturing method of claim 6, wherein it comprises:
a) contacting the composition for silicon-containing dielectric film deposition with a substrate to adsorb the composition for silicon-containing dielectric film deposition in the substrate;
b) purging the remaining composition for silicon-containing dielectric film deposition and by-products;
c) forming an atomic layer having a Si—N bond by injecting reaction gas into the substrate containing the adsorbed composition for silicon-containing dielectric film deposition to remove a ligand of the composition for silicon-containing dielectric film deposition; and
d) purging the remaining reaction gas and reaction by-products.

8. The manufacturing method of claim 7, wherein the reaction gas is supplied after being activated by generating plasma of 100 to 1000 W.

9. The manufacturing method of claim 8, wherein the reaction gas is supplied after being activated by generating plasma of 100 to 500 W.

10. The manufacturing method of claim 9, wherein a substrate temperature is 100 to 600° C.

11. The manufacturing method of claim 9, wherein the reaction gas is supplied at a flow rate of 100 to 10000 sccm.

12. The manufacturing method of claim 9, wherein step a) is performed at a pressure of 0.05 to 10 torr, and step c) and step c') are performed at a pressure of 0.05 to 30 torr.

13. The manufacturing method of claim 6, wherein it comprises:
a) contacting the composition for silicon-containing dielectric film deposition with a substrate to adsorb the composition for silicon-containing dielectric film deposition in the substrate;
b) purging the remaining composition for silicon-containing dielectric film deposition and by-products;
c') forming an atomic layer having a Si—N bond by generating plasma while injecting reaction gas to remove a ligand of the composition for silicon-containing dielectric film deposition;
and
d) purging the remaining reaction gas and reaction by-products.

14. The manufacturing method of claim 7, wherein the reaction gas is supplied after being activted by generating plasma of 100 to 400 W.

15. The manufacturing method of claim 14, wherein a substrate temperature is 100 to 600° C.

16. The manufacturing method of claim 14, wherein step a) is performed at a pressure of 0.05 to 10 torr, and step c) is performed at a pressure of 0.05 to 30 torr.

* * * * *